United States Patent [19]

Daumas

[11] 4,058,574

[45] Nov. 15, 1977

[54] PROCESS FOR THE OXYCHLORINATION OF HYDROCARBONS WITH AMMONIUM CHLORIDE

[75] Inventor: Jean-Claude Daumas, Orsay, France

[73] Assignee: Rhone-Progil, Paris, France

[21] Appl. No.: 606,885

[22] Filed: Aug. 22, 1975

Related U.S. Application Data

[63] Continuation of Ser. No. 378,071, July 11, 1973, abandoned.

[30] Foreign Application Priority Data

July 11, 1972 France .................................. 72.25070

[51] Int. Cl.² .............................................. C07C 17/15
[52] U.S. Cl. ............................ 260/659 A; 260/654 R; 260/654 A; 260/656 R; 260/659 R
[58] Field of Search .......... 260/659 A, 656 R, 654 A, 260/659 R, 654 R

[56] References Cited

U.S. PATENT DOCUMENTS

| 3,159,455 | 12/1964 | Skaperdas et al. .......... 260/659 A X |
| 3,363,010 | 1/1968 | Schwarzenbek ............ 260/659 A X |
| 3,634,330 | 1/1972 | Michel et al. ................ 260/659 A X |
| 3,679,373 | 7/1972 | Vancamp et al. ........... 260/659 A X |
| 3,849,338 | 11/1974 | Daumas et al. ............. 260/659 A X |

FOREIGN PATENT DOCUMENTS

46-37323  2/1971  Japan ................................ 260/659 A

*Primary Examiner*—Charles F. Warren

[57] ABSTRACT

The invention is addressed to the manufacture of chlorinated hydrocarbons by catalytic oxychlorination, in which the chlorine is derived, at least in part, from ammonium chloride, and in which a suitable catalyst comprises a support formed of silica and magnesium with a catalytic active portion formed of copper chloride and an alkali metal chloride. Such catalysts give good yields, little combustion of hydrocarbons and low impurities.

12 Claims, No Drawings

PROCESS FOR THE OXYCHLORINATION OF HYDROCARBONS WITH AMMONIUM CHLORIDE

This is a continuation of application Ser. No. 378,071, filed July 11, 1973, now abandoned.

This invention relates to the manufacture of chlorinated hydrocarbons by catalytic oxychlorination of hydrocarbons, in which chlorine is made available, at least in part, from ammonium chloride.

The manufacture of chlorinated hydrocarbons, by catalytic oxychlorination, with chlorine derived from hydrochloric gas, is well known. It is possible, in this way, to attain various chlorinated solvents as well as dichloroethane, a precursor for vinyl chloride.

Moreover, in the industrial manufacture of sodium carbonate from sodium chloride, it is well known that if the ammonia is recovered and recycled from the ammonium chloride that is produced, the corresponding chlorine is partially lost since it combines as calcium chloride which is difficult to use.

For a long time, suggestions have been made to find suitable markets for ammonium chloride, for example, as a fertilizer, or to retrieve the chlorine through various processes. More recently, it has been proposed to make use of ammonium chloride as a chlorinating agent in the catalytic oxychlorination of hydrocarbons, with the recovery of ammonia that is liberated. Utilization of ammonium chloride has been taught in the U.S. Pat. No. 3,159,455 which, in a general way, is concerned with the oxychlorination of hydrocarbons but which gives no precise details for manufacture specifically adapted to the use of ammonium chloride, the reactivity of which is less than that of hydrochloric acid, when used as a source of chlorine.

To select a process which makes use of ammonium chloride as a source of chlorine in the oxychlorination of hydrocarbons, a complete review has been made of all of the elements of the process, and particularly with respect to the catalyst used. French Pat. No. 1,505,045 describes the use of conventional catalysts for oxychlorination by means of hydrochloric acid and indicates yields obtained with the use of the catalyst embodying silica gel as the support, but in which the yields are not very good.

When used at temperatures higher than those generally employed in oxychlorination, slightly above 200° C., because of the weak reactivity of an ammonium chloride, such catalysts have low stability and are unsuitable for continued use over long periods of time. Finally, more recent patents indicate results obtained by means of a catalyst having a support of alumina with low specific surfaces, and which are no longer suitable.

It has now been found that good results, from the standpoint of yield, loss through combustion, impurities, and long catalyst life can be obtained by means of a catalyst formed with a support composed principally of silica and magnesia, with the catalytic active components being composed, at least in part, of copper chloride and an alkali metal chloride.

Catalysts of this type have been described in the French Pat. No. 1,579,562 and in U.S. Pat. No. 3,849,338 Such catalysts are advantageously obtained by calcination of silica hydrogel containing suitable compounds of magnesium, such as magnesium nitrate or magnesium chloride, at temperatures suitable for obtaining the active surfaces desired.

Such catalysts normally can be employed as described in the French Pat. No. 1,579,562 previously referred to, for nonselective oxychlorination of hydrocarbons by means of hydrochloric gas as a source of chlorine. The variety of chlorinated hydrocarbons capable of being produced, is controlled principally by proper selection of a sufficiently high temperature, which does not involve excessive destruction of the treated hydrocarbons through combustion. It has been found, unexpectedly, that such catalysts, when used with ethylene and ammonium chloride, as a source of chlorine, selectively produces 1:2-dichloroethane and almost entirely avoids the formation of such compounds as chloroform and carbon tetrachloride which interfere with the subsequent uses of dichloroethane. The proportion of nitrogen oxides produced remains desirably low.

In the catalyst particularly suitable for the process of this invention, the supports are formed of silica and magnesia having a specific surface of 50 to 180 $M^2/g$, with the proportion of magnesia being with the range of 5 to 30 percent by weight of the calcined support. Copper, common to this type of catalyst, can be employed in an amount within the range of 2 to 7 percent by weight in relation to the final catalyst. The atomic ratio of alkali metal to copper is quite critical and preferably is within the range of 0.3 to 1.3. Potassium is the preferred alkali metal.

A certain number of other components can be added to the catalyst, such as rare earths or alumina, but the results obtained do not justify the added complications for the preparation of catalysts with such added materials.

These catalysts, having supports made up of silica and magnesia permit the use of reaction temperatures as high as 200° C. to 380° C., but preferably below 340° C., with contact times which cannot be very long, up to not more than about one second, but which, nevertheless, can be longer. From the standpoint of industrial use, it is desirable to select working temperatures as low as possible but still compatible with other characteristics of operation, and principally with the acceptable rates of recycling. In this way, the combustion of treated hydrocarbons as well as the formation of hydrogen oxides from liberated ammonia, can be kept very low.

It will be understood that these catalysts can be used for oxychlorination reaction of hydrocarbons with mixtures of hydrochloric gas and ammonium chloride with the result intermediate those obtained with hydrochloric gas alone and with ammonium chloride alone, from the standpoint of the proportions of the various chlorinated hydrocarbons produced.

Oxychlorination between the catalyst and the gaseous components, wherein chlorine is carried off, at least in part, by the ammonium chloride, can be carried out by all of the procedures currently in use, especially in a fixed bed catalyst, mobile bed or fluid bed catalyst, and under various pressures. Further, as is well known, it is possible to dilute the catalyst by means of various inactive materials, as well as the gases as by means of inert diluents or steam.

In order to illustrate the present invention, a number of examples will hereinafter be given by way of illustration, but not by way of limitation, with catalysts embodying the features of this invention as well as with catalysts previously recommended for purposes of comparison.

All of the tests were carried out in a fluidized bed with a laboratory reactor having a diameter of 20 mm., containing 25 CM³ of catalyst, in which the reactor is electrically heated by coils to achieve the thermal gradient necessary to avoid condensation of ammonium chloride.

This reactor was fed with ethylene and air processed through a sublimation zone of the ammonium chloride.

At the outlet of the reactor, the nontransformed ammonium is recovered in crystallized form, as well as the final fluid and gaseous ethylenes for chromatographic analysis.

The operating conditions are as follows:
$R_1$, molecular ratio $O_2/C_2H_4$
$R_2$, molecular ratio $NH_4Cl/C_2H_4$
T, temperature of the test in ° C.
θ, time of contact in seconds These are calculated in accordance with the following equations:

$X_g$, rate of conversion of the ethylene =

$$100 \frac{\text{Moles } C_2H_4 \text{ transformed}}{\text{Moles } C_2H_4 \text{ introduced}}$$

$Y_g$, rate of conversion of the ammonium chloride =

$$100 \frac{\text{Moles } NH_4Cl \text{ transformed}}{\text{Moles } NH_4Cl \text{ introduced}}$$

$XNH_3$, rate of conversion of the ammonia in nitrogen oxides =

$$100 \frac{\text{Moles } NH_3 \text{ transformed}}{\text{Moles } NH_3 \text{ produced}}$$

$XCO_2$, rate of combustion of ethylene =

$$100 \frac{\text{Moles of } CO_2 \text{ formed}}{\text{Moles } C_2H_4 \text{ introduced}}$$

Finally, various selected compounds, 1,2-dichloroethane, carbon tetrachloride 1,1,2-trichloroethane and vinyl chloride, identified as $S_1$, $S_2$, $S_3$ and $S_4$ respectively, are defined in the ratio between the number of molecules of the respective compound to the number of molecules of transformed ethylene.

EXAMPLE 1

This example gives the results obtained with different catalysts having supports made up either with silica gel to which magnesia has been added together in accordance with the process of this invention, or of silica alone or alumina alone, the latter for various reasons are not suitable, although being currently used in oxychlorination.

Besides copper, all of the catalysts contain potassium chloride as their active component in the ratio (K)/(Cu), calculated in atoms, equal to 0.6. This is a value selected as suitable for many oxychlorination catalysts containing alkali metals.

The grain size within the range of 100 to 200 microns was selected for all catalysts together as suitable for the laboratory tests.

The supports formulated of silica were in the form of microballs of silica gel, obtained by coagulation of droplets of silica sol in a liquid nonmiscible with water. The supports made up of silica and magnesia were in the form of the same microballs with the silica gel impregnated with magnesium nitrate such that, after calcining, the amount of magnesia represented 20 percent by weight of the support. The supports fabricated of active alumina were in the form of small particles obtained through rapid dehydration of the hydroargilite in a current of warm gases.

All of the tests were carried out at a temperature T of 360° C. and with a contact time of one second. The ratios $R_1$ and $R_2$ equal to 0.7 and 1.5, respectively, were selected as suitable for obtaining interesting results with different catalysts. The temperature of 360° C. was arbitrarily selected as high enough to maximize the combustion and the formation of nitrogen oxides, to facilitate comparison.

Table 1 gives the characteristics of the different catalysts which were used, the results obtained, as well as observations concerning the production of other compounds.

From Table 1 it will be seen that the catalyst giving the best results are the first four. Their activity, in measured amounts of $X_g$ and $Y_g$ is large and sufficient, although less than that of catalyst 6, the results of which were obtained on account of the nature and the surface of the support. At the same time, the catalyst having a support of alumina gives too much combustion and too much chloroform. The first four catalysts give little nitrogen oxides and low combustion and, moreover, are very selective in the production of 1,2-dichloroethane. By comparison, catalyst 5, on silica alone, is only slightly active, slightly selective and causes appreciably greater combustion of hydrocarbon than the first four catalysts. The use of supports having a silica base makes the catalyst more resistant to abrasion than catalysts formulated of an alumina base.

EXAMPLE 2

This example concerns tests carried out at various temperatures with catalysts corresponding to catalyst No. 3 of the preceding example, for the value of 0.7 for the ratio $R_1$, and the two values of 0.7 and 1 for the ratio $R_2$.

The results are given in Table 2.

The results show that it is advantageous to work with relatively low temperatures so that the formation of nitrogen oxides ($X_{NH3}$) and combustion ($X_{CO2}$) are held to the lowest possible values. However, the rate of conversion of ammonium chloride, at these temperatures, is still sufficient ($Y_g$).

EXAMPLE 3

This example is intended to show the influence of the specific surface of the supports for the catalyst. The conditions of the tests are the same as those of Example 1. In Table 3 the results are concerned with catalysts previously used on supports having a specific surface of 70, 120, and 150 M2/g, respectively, and with another one on a support having a specific surface of 270 M2/g; all catalysts have the same content of copper (3.5%) and potassium (ratio K/Cu - .06) so that only the specific surface was the variable. These supports were fabricated of silica and magnesia, with the magnesia present in the amount of 20 percent by weight of the support.

These results showed the tendency for the increase in the rate of combustion ($XCO_2$) when the specific surface of the support increases without increasing activity of the catalyst. As a result, when the values of the other parameters are taken into account, it is deemed desirable to maintain the specific surface of the supports at a sufficiently low value.

EXAMPLE 4

This example brings together several results obtained with catalysts in which the ratio (K)/(Cu) is varied under the test conditions of No. 1. The determination of this ratio in each particular case is significant since the activity of the catalyst depends upon the ratio quite strongly. These catalysts all contain 3.5% by weight copper on supports of silica and magnesia having a specific surface of 120 M2/g containing 20 percent by weight magnesia. Table 4 sets forth the results obtained. Again, catalysts 3 of Example 1 (line 2 of the table) indicates superiority. When reference is made herein to copper and potassium or other alkali metal, reference to the corresponding chloride is intended.

This table shows that the activity of the catalyst rises to a maximum in function at a ratio of (K)/(Cu) of 0.6 (values of the ratios $X_g$ and $Y_g$). It will be understood that changes may be made and the details of the formulation and operation without departing from the invention in the following claims.

TABLE 1

| CATALYST N° | Support | %Cu | $X_g$ | $Y_g$ | $X_{NH_3}$ | $XCO_2$ | $S_1$ | $S_2$ | $S_3$ | $S_4$ | OBSERVATIONS |
|---|---|---|---|---|---|---|---|---|---|---|---|
| 1 | Silica Magnesia 70 m²/g | 3,5 | 34,0 | 44,0 | 0,1 | 0,1 | 95,0 | 0,7 | 1,7 | 1,5 | |
| 2 | Silica Magnesia 120 m²/g | 5 | 32,2 | 44,0 | 0,1 | 0,3 | 92,8 | 1,4 | 1,7 | 2,2 | Poor |
| 3 | Silica Magnesia 120 m²/g | 3,5 | 35,0 | 48 | 0,1 | 0,2 | 94,0 | 1,3 | 1,7 | 2,0 | formation |
| 4 | Silica Magnesia 150 m²/g | 3,5 | 35,0 | 47,5 | 0,1 | 0,3 | 93,5 | 1,5 | 1,6 | 2,1 | of |
| 5 | Silica 200 m²/g | 15 | 29,6 | 38,5 | 0,05 | 0,5 | 89.6 | 0,7 | 1,6 | 6,3 | chloroform |
| 6 | Alumina 158 m²/g | 7 | 39,0 | 53,7 | 0,05 | 0,7 | 88,4 | 2,9 | 1,5 | 4,2 | Significant amount of chloroform |

TABLE 2

| RATIO $R_1$ AND $R_2$ | T° C | $X_g$ | $Y_g$ | $X_{NH_3}$ | $X_{CO_2}$ | $S_1$ | $S_2$ | $S_3$ | $S_4$ |
|---|---|---|---|---|---|---|---|---|---|
| $R_1 = 0,7$ | 320 | 18,6 | 53,5 | 0,8 | 0,04 | 97,0 | 0,8 | 0,5 | 1,4 |
| | 340 | 21,5 | 61,6 | 3,3 | 0,3 | 95,8 | 0,8 | 0,6 | 1,2 |
| $R_2 = 0,7$ | 360 | 21,4 | 59,8 | 7,6 | 0,5 | 92,1 | 0,9 | 0,9 | 3,2 |
| | 380 | 21,7 | 60,0 | 2,6 | 0,7 | 87,0 | 1,0 | 1,8 | 6,4 |
| $R_1 = 0,7$ | 320 | 14,1 | 23,6 | 0 | 0,04 | 93,0 | 1,1 | 0,8 | 1,6 |
| | 340 | 24,2 | 48,9 | 0,2 | 0,2 | 95,5 | 1,0 | 1,0 | 1,5 |
| $R_2 = 1,0$ | 360 | 27,5 | 55,0 | 0,5 | 0,3 | 94,0 | 1,0 | 1,6 | 2,0 |
| | 380 | 27,5 | 53,3 | 1,4 | 0,3 | 84,2 | 1,3 | 2,0 | 10,7 |

TABLE 3

| Surface m2/g | $X_g$ | $Y_g$ | $X_{NH_3}$ | $X_{CO_2}$ | $S_1$ |
|---|---|---|---|---|---|
| 70 | 34,0 | 44,0 | 0,1 | 0,1 | 95,0 |
| 120 | 35,0 | 48,0 | 0,1 | 0,2 | 94,0 |
| 150 | 35,0 | 47,5 | 0,1 | 0,3 | 93,5 |
| 270 | 34,0 | 46,4 | 0,1 | 0,8 | 91,1 |

TABLE 4

| K/Cu in atoms | $X_g$ | $Y_g$ | $X_{NH_3}$ | $X_{CO_2}$ | $S_1$ |
|---|---|---|---|---|---|
| 0,3 | 31 | 40 | 0,1 | 0,5 | 92 |
| 0,6 | 35 | 48 | 0,1 | 0,2 | 94 |
| 1,3 | 32 | 42 | 0,1 | 0,15 | 95 |

I claim:

1. A process for the catalytic oxychlorination of hydrocarbons with chlorine derived at least in part from ammonium chloride comprising contacting a gaseous mixture containing a hydrocarbon, ammonium chloride and an oxygen-containing gas with a catalyst of copper chloride and an alkali metal chloride on a support consisting essentially of silica and magnesia at a temperature within the range of 200° to 380° C.

2. A process as claimed in claim 1 in which the support has a specific surface area within the range of 50 to 180 M²/g.

3. A process as claimed in claim 1 in which the amount of magnesia is within the range of 5 to 30 percent by weight of the support.

4. A process as claimed in claim 1 in which the ratio of alkali metal atoms to copper atoms in the catalyst is within the range of 0.3 to 1.3.

5. A process as claimed in claim 1 in which the alkali metal chloride is potassium chloride.

6. A process as claimed in claim 1 in which the amount of copper in the catalyst is within the range of 2 to 7 percent by weight.

7. A process as claimed in claim 1 in which the support is prepared by impregnating silica hydrogel with a magnesium compound that is convertible to magnesia upon calcination, and then calcining the impregnated hydrogel.

8. A process as claimed in claim 7 in which the silica is initially in the form of microballs of silica hydrogel.

9. A process for the catalytic oxychlorination of hydrocarbons with chlorine derived at least in part from ammonium chloride comprising contacting a gaseous mixture containing a hydrocarbon, ammonium chloride and an oxygen-containing gas with a catalyst of copper chloride and an alkali metal chloride on a support consisting essentially of silica and magnesia prepared by impregnating a silica hydrogel with a magnesium compound convertible to magnesia upon calcination, and then calcining the impregnated hydrogel, at a temperature within the range of 200° to 380° C.

10. A process for the catalytic oxychlorination of ethylene with chlorine derived at least in part from ammonium chloride comprising contacting a gaseous mixture containing ethylene, ammonium chloride and an oxygencontaining gas with a catalyst of copper chloride and an alkali metal chloride on a support consisting essentially of silica and magnesia at a temperature within the range of 200° to 380° C.

11. A process for the catalytic oxychlorination of ethylene with chlorine derived at least in part from ammonium chloride comprising contacting a gaseous mixture containing ethylene, ammonium chloride and an oxygen-containing gas with a catalyst of copper chloride and an alkali metal chloride on a support consisting essentially of silica and magnesia prepared by impregnating a silica hydrogel with a magnesium compound convertible to magnesia upon calcination, and then calcining the impregnated hydrogel, at a temperature within the range of 200° to 380° C.

12. A process for the catalytic oxychlorination of ethylene to form 1,2-dichloroethane with chlorine derived at least in part from ammonium chloride comprising contacting a gaseous mixture containing ethylene, ammonium chloride and an oxygen-containing gas with a catalyst of copper chloride and an alkali metal chloride, with the atomic ratio of alkali metal to copper being within the range of 0.3 to 1.3, on a support consisting essentially of silica and magnesia, with the magnesia being present in an amount within the range of 5 to 30% based upon the total weight of the support, at a range of 200° to 380° C and a contact time for at least one second.

* * * * *

UNITED STATES PATENT OFFICE
CERTIFICATE OF CORRECTION

Patent No. 4,058,574            Dated November 15, 1977

Inventor(s) JEAN-CLAUDE DAUMAS

It is certified that error appears in the above-identified patent and that said Letters Patent are hereby corrected as shown below:

IN THE SPECIFICATION

Column 5, in Table 1 under " 6 Alumina ", delete "158 $m^2/g$" and insert therefor -- 150 $m^2/g$ --.

Column 5, in Table 2 under the column designated "Yg" (fifth number under that column), delete "23,6" and insert therefor -- 28,6 --.

Column 5, in Table 2 under the column designated "$X_{NH_3}$" (fourth number under that column), delete "2,6" and insert therefor -- 9,6 --.

Column 5, in Table 2 under the column designated "$S_1$" (fifth number under that column), delete "93,0" and insert therefor -- 96,0 --.

Signed and Sealed this

Seventh Day of March 1978

[SEAL]

Attest:

RUTH C. MASON      LUTRELLE F. PARKER
*Attesting Officer*      *Acting Commissioner of Patents and Trademarks*